United States Patent
Grez et al.

(10) Patent No.: US 6,918,300 B2
(45) Date of Patent: Jul. 19, 2005

(54) SYSTEM AND METHOD FOR DETERMINING THE RESONANT FREQUENCY AND/OR AMPLITUDE OF AN OSCILLATING APPLIANCE SUCH AS A POWER TOOTHBRUSH

(75) Inventors: Joseph W. Grez, Snoqualmie, WA (US); Kurt E. Steinke, Bellevue, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 66 days.

(21) Appl. No.: 10/179,709

(22) Filed: Jun. 24, 2002

(65) Prior Publication Data

US 2003/0233877 A1 Dec. 25, 2003

(51) Int. Cl.$^7$ .............................................. G01N 29/06
(52) U.S. Cl. .............................. 73/579; 73/578; 73/649
(58) Field of Search ........................ 73/579, 597, 598, 73/600, 602, 578, 630, 646, 649, 584, 593, 599, 668, 1.82, 576; 318/114, 128, 104; 15/22.1

(56) References Cited

U.S. PATENT DOCUMENTS

| 5,027,285 | A | * | 6/1991 | McCartney et al. .......... 702/58 |
| 5,150,492 | A | * | 9/1992 | Suroff ........................ 15/22.1 |
| 5,189,751 | A | * | 3/1993 | Giuliani et al. .............. 15/22.1 |
| 5,263,218 | A | * | 11/1993 | Giuliani et al. .............. 15/22.1 |
| 5,305,492 | A | * | 4/1994 | Giuliani et al. ............. 15/176.1 |
| 5,369,980 | A | * | 12/1994 | Kocache ..................... 73/25.02 |
| 5,378,153 | A | * | 1/1995 | Giuliani et al. ............. 433/216 |
| 5,613,259 | A | * | 3/1997 | Craft et al. .................. 15/22.1 |
| 5,754,016 | A | | 5/1998 | Jovanovic et al. .......... 318/118 |
| 6,391,042 | B1 | * | 5/2002 | Cimino ...................... 606/169 |
| 6,441,571 | B1 | * | 8/2002 | Ibuki et al. ................. 318/114 |
| 2002/0092104 | A1 | * | 7/2002 | Ferber et al. |
| 2003/0115693 | A1 | * | 6/2003 | Grez et al. |

FOREIGN PATENT DOCUMENTS

| EP | 0791969 A1 | 8/1997 |
| EP | 1096660 A2 | 5/2001 |
| EP | 1117176 A2 | 7/2001 |
| WO | 95/33419 | 12/1995 |

* cited by examiner

*Primary Examiner*—Hezron Williams
*Assistant Examiner*—Jacques M. Saint-Surin

(57) ABSTRACT

A system and corresponding method for determining the frequency and/or amplitude of an oscillating apparatus, which includes a driving assembly having a stator portion and an armature portion, and a driving signal circuit which supplies a driving signal to the stator portion. A control circuit interrupts the drive signal momentarily, for at least a quarter of a cycle, at periodic intervals, resulting in a signal being induced into the stator coil from continuing movement of the armature. A measurement/read circuit is connected to the stator coil for determining one or both of the frequency of the induced signal and the amplitude of the induced signal. The frequency or amplitude information is then compared against pre-established values and any differences are used to change the driving signal so as to provide maximum performance of the appliance.

16 Claims, 2 Drawing Sheets

SYSTEM AND METHOD FOR DETERMINING THE RESONANT FREQUENCY AND/OR AMPLITUDE OF AN OSCILLATING APPLIANCE SUCH AS A POWER TOOTHBRUSH

TECHNICAL FIELD

This invention relates generally to the determination of the resonant frequency and/or amplitude of an oscillating appliance such as a power toothbrush, and more specifically concerns such a system which does not require a separate sensor to accomplish such a determination.

BACKGROUND OF THE INVENTION

In resonant oscillating systems, such as found in many small appliances, including power toothbrushes, it is important that the drive frequency be quite close to the natural resonant frequency of the system for proper, efficient operation. The operation of such resonant frequency systems, however, can be significantly influenced by dynamic operational factors, including changes in loading on the device, e.g. loading of the brushhead in a power toothbrush, changes in the operating state of the power supply, i.e. the battery, and changes in performance of various components of the device due to aging or other factors. For instance, the resonant frequency of the system and the amplitude of movement of the device workpiece such as, for instance, a brushhead, can be affected by such changes.

One of the ways to accomplish a close match between the drive frequency for the device and the natural resonant frequency of the system-as well as maintaining performance of the device in the face of operating changes, such as those noted above, is to tightly control the tolerances of the system components. This approach, however, is expensive, and also may not provide a capability for compensating for changes in the system, either dynamic (short term), such as, for instance, changes in loading, or more permanent/long term, such as aging of the components.

An alternative approach is to use a sensing system which reads, i.e., determines, the actual operating frequency of the device and/or amplitude of movement of the workpiece during operation of the device and adjusts the frequency and power of the drive signal accordingly. U.S. Pat. No. 5,613,259 is an illustration of such an approach. However, the '259 approach requires a separate sensing system to monitor performance of the device and provide a signal to correct/change the drive signal accordingly. The separate sensing system adds expense to the device as well as complexity. Accordingly, it is desirable to have a sensing system which can make determinations of operational frequency and amplitude without the need for a separate sensing element.

SUMMARY OF THE INVENTION

Accordingly, the present invention is a system and corresponding method for determining the resonant frequency and/or amplitude of an oscillating appliance, such as a toothbrush, having a drive assembly with a stator portion and an armature portion and a circuit for supplying a driving signal to the stator portion, comprising: a control circuit for temporarily interrupting the driving signal from the stator portion of the drive assembly for a selected period of time, such that a sufficient signal is induced into the stator by continuing movement of the armature following interruption of the driving signal that the frequency and/or amplitude of the induced signal can be determined; and a measurement circuit for determining at least one of: (1) the frequency of the induced signal, and (2) the amplitude of the induced signal, wherein the induced signal provides useful information concerning operation of the appliance.

BEST MODE FOR CARRYING OUT THE INVENTION

Figure 1:
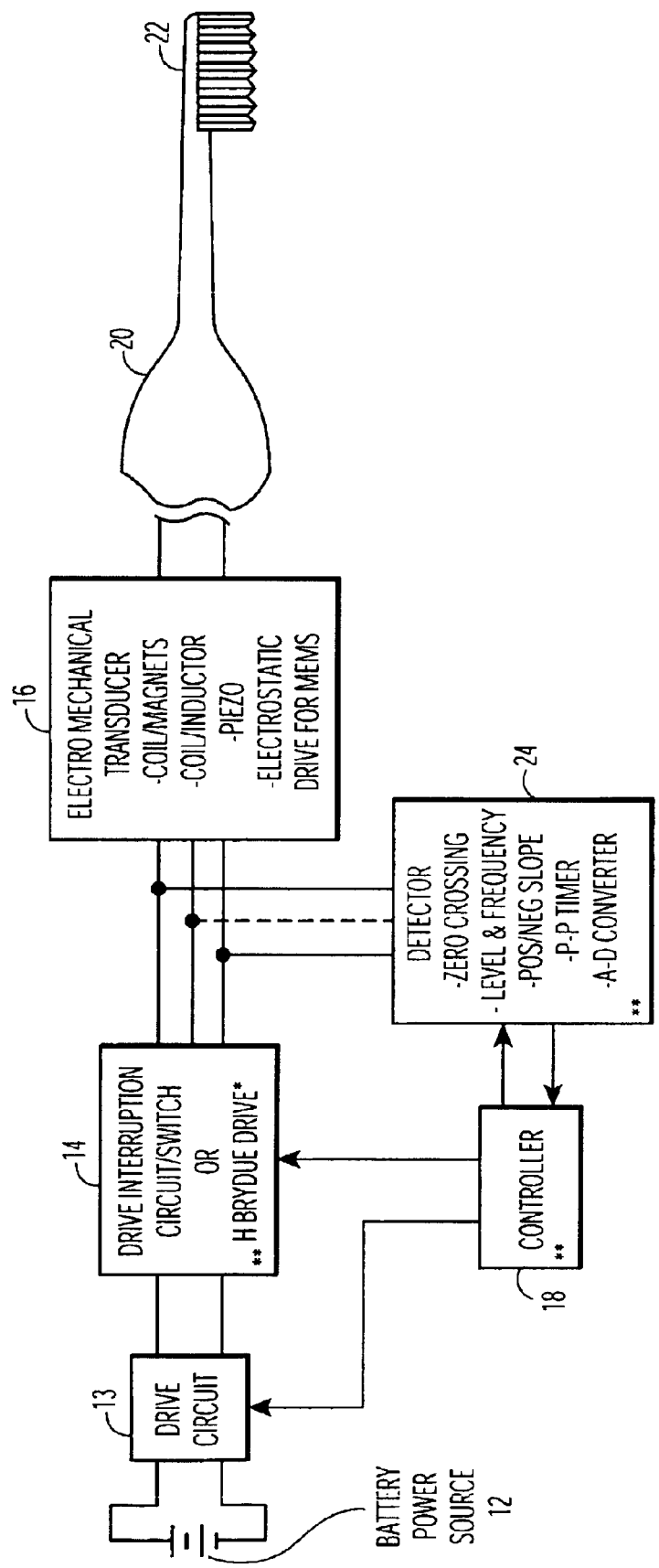
FIG. 1 is generalized block diagram of the system of the present invention.

The present invention is used with a resonant operating/drive system for a small appliance, such as a power toothbrush, which includes a motor assembly with a stator coil to which a drive signal is applied, and an armature which moves or rotates in response to the drive signal flowing through the stator coil. The workpiece, i.e. a brushhead, is mounted on the end of the armature or a shaft driven by the armature. Typically, the drive signal will be in the form of a square wave or sine wave which produces the desired movement of the armature.

In the present invention, in general, the drive signal applied to the stator will be interrupted at pre-selected intervals for a brief time, typically approximately one cycle. The armature, however, will continue to move after the drive signal has been interrupted in an underdamped or undamped system. The movement of the armature and the magnets thereon induces a back EMF in the stator coil. This induced signal will be close to a sine wave, when the drive signal is a square wave, for a high Q system. The induced signal is closely representative of the frequency and amplitude of the workpiece movement. Accurate information concerning the operation of the device is thus provided by the induced signal. When the drive signal is interrupted, a "read" circuit is connected to the stator coil. The signal which is induced back into the stator coil, during the time that the drive signal is interrupted or disconnected from the stator coil, is measured by the read device, for frequency and/or amplitude; in some cases, additional information, as described below, is obtained from the signal.

The frequency and/or amplitude of the induced signal can be determined in various ways. Those values, however, are determined without the necessity of a separate sensing element or member, since the motor armature and stator are part of the device itself. The frequency and/or amplitude of the signal are then compared with established values of frequency and amplitude. The differences can then be used to adjust the frequency and/or amplitude of the drive signal, so as to bring the drive signal frequency/amplitude into conformance with the actual resonant frequency/desired amplitude of the system. This is a dynamic correction system; it enables the relaxing of the operating tolerances of the components of the device without affecting performance thereof, since those differences can be accommodated by adjusting the frequency/amplitude of the drive signal.

One application of the system of the present invention is a power toothbrush. The invention, however, can be used in other applications, including other small appliances, as well as in other systems where the relationship of the drive frequency to the natural resonant frequency of a driven device is important for proper and efficient operation. In the context of a power toothbrush, the drive system typically involves a motor of some kind. The motor could be an electromagnetic device involving an e-shaped drive coil and a pivoting lever arm with permanent magnets located on a rear end thereof, such as shown in U.S. Pat. Nos. 5,378,153 and 5,189,751; it could also be a rotary motor involving a stator coil and an armature (drive shaft) which rotates through a selected arc. Basically, such various systems can be broadly characterized by the term electromechanical transducer, which converts electrical energy provided by a drive signal to a mechanical workpiece movement.

Generally, the devices which are suitable for use with the present invention will include a stator coil to which the drive signal is applied and an armature which moves under the influence of the stator coil. At the free end of the armature or extension thereof is secured a workpiece element such as a toothbrush brushhead.

Figure 2:
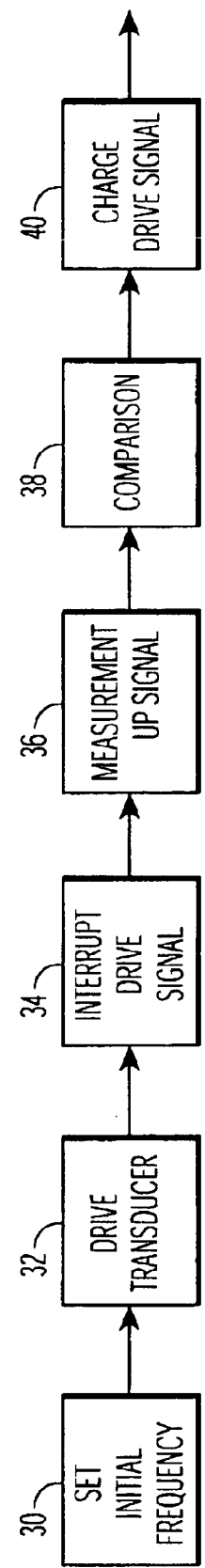
FIG. 2 is a block diagram showing the method steps carried out by the present invention.

The system of the present invention is illustrated in one embodiment in FIG. 1, with FIG. 2 representing the specific steps carried out by the present system.

FIG. 1 shows a block form generalized system which includes a battery power source 12, and a drive interruption circuit/switch 14, which is different than the mechanical on-off switch for the device (not shown). The battery 10 supplies the power to a drive signal circuit 13, which produces a drive signal for the electromechanical transducer (the motor) 16 through the interruption circuit 14 by action of controller 18. The transducer 16 will include an output assembly, generally at 20, which includes the workpiece mounted for movement thereon. The output assembly could, for example, be a brushhead assembly for a power toothbrush.

The electromechanical transducer 16 can have a number of different embodiments, including a coil/permanent magnet arrangement, such as shown in the '153 and '751 patents, a coil/inductor arrangement, a piezoelectric transducer, and a electrostatic drive assembly. Normally, transducer 16 will, upon activation by the device on-off switch, operate until stopped either by a timing device (not shown) or deactivation by the device on-off switch.

The electromechanical transducer 16, is part of the resonant operating system. It operates in response to a drive signal from a circuit 13 to produce a workpiece having a back/forth movement. A resonant system is designed so that the drive frequency is approximately the same as the natural resonant frequency of the system. However, for various reasons, the natural resonant frequency may be actually different than the drive frequency, such as because of differences in components, or dynamic changes occurring during use of the appliance. In the present invention, a drive signal interrupter circuit 14 is positioned between the drive signal circuit 13 battery and the electromechanical transducer 16. The drive signal interrupter circuit 14 is designed to interrupt the drive signal which is applied to the stator coil of the electromechanical transducer, under the control of control circuit 18. Typically, the interruption will last for a short time, usually on the order of one-half cycle to one cycle, although one-quarter cycle may be sufficient, and it could be longer, depending upon the particular application and the information which is to be obtained relative to the induced signal. It must be enough that the frequency and/or amplitude of the induced signal can be determined. The drive signal interruption can occur at selected intervals, controlled by a timer in controller 18. The interval, i.e. sampling rate, can vary widely, but typically might be 3–10 times per second for a toothbrush application. It could be less frequently, even once per usage, if compensation is to be made for conditions like temperature, brush wear and brush aging. It could be more frequently for conditions such as brushing pressure, as long as performance of the brush is not significantly affected.

When controller 18 interrupts the drive signal to the stator portion of transducer 16, the armature portion thereof will typically continue to move, in an undamped or underdamped system, resulting in a back EMF signal being established in the stator coil. If the system is overdamped, then the present invention will typically not be used since the induced signal, if any, would not be representative of the operating action of the device.

When the drive signal is interrupted, a detector element 24 is operatively connected to the stator member. Detector 24 will read the signal induced in the stator coil by action of the armature. Once the signal has been obtained, a determination is then made as to the frequency of the induced signal and/or the amplitude of the induced signal, or other performance information obtained. The frequency of the signal can be determined in various conventional ways. These include different "single point" techniques, i.e., the evaluation of single points on the induced signal waveform, including conventional zero crossing, peak value, reference voltage (selected voltage level) crossing or similar slope circuits. These circuits are all well known for frequency determination for a given waveform and hence are not discussed in detail herein.

The detector current 24 is also capable of reading the amplitude of the induced signal in the stator coil by simply determining the peak value thereof. In some embodiments, only the frequency will be determined, while in others both frequency and amplitude will be determined.

Alternatively, the analog data obtained by the detector can be converted to digital values. The digital data can then be evaluated for signal damping factors affecting performance, including damping time and system Q. Such an evaluation provides additional information concerning the actual dynamic operation of the system. The entire waveform can be digitized and then "fitted" against a sine wave reference signal, providing specific information about the induced signal, including amplitude information, the angular velocity of the damped oscillators of the signal, as well as Q of the system and damping time.

The detector 24 or the controller circuit 18, which will include a microprocessor, will then in operation compare the induced signal from the stator coil against a pre-selected desired frequency and/or amplitude, or digitized waveform. Any differences so determined are then used to change the operating frequency/amplitude or perhaps other characteristics of the drive signal from circuit 13. This results in a closer match between the drive signal and the actual operation of the device, in terms of frequency, amplitude and other performance values, e.g., damping. The interrupter circuit 14 is then disabled and the revised drive signal is again connected to the stator portion of the transducer (motor) 16. For instance, the drive signal frequency can be changed to match the actual natural resonant frequency of the system at that point in time. Further, the amplitude of the drive signal can be changed to produce a desired amplitude of movement of the workpiece, e.g. brushhead 22.

FIG. 2 shows the sequential steps of the method carried out by the system described above. First, for the example of frequency adjustment, as shown in block 30, an initial drive frequency for the device is established, such as during testing at the factory. As one example, for a toothbrush with a natural resonant frequency of 261 Hz, the drive frequency is selected to be within at least 15 Hz relative to the target natural resonant frequency of the device. In the next step, at block 32, the transducer, i.e. the motor assembly, will be initially driven and allowed to stabilize for a selected period of time; for the above toothbrush, 150 milliseconds will be sufficient for the time of stabilization. The initial drive frequency generally is chosen to be within 5–10% of the resonant frequency of the desired resonance mode of the system. It must be close enough to excite the desired resonance mode noticeably. If the initial frequency is too far removed, little or no amplitude gain could occur and there will be only a small signal induced in the stator, if any.

In the next step, the drive signal is interrupted, as shown at block 34, for a selected period of time, such as one cycle. In the next block 36, measurement is made of the induced signal. The measurement will include frequency, for the present example, but could also include amplitude or other factors, such as Q of the system or damping. These analog measurements can be compared against standard values and any differences determined, or the analog values could be converted to digital values for comparison, including comparison of one or more cycles of the complete induced waveform with the established values or waveform.

The differences resulting from the comparison will then be used to change the characteristics of the drive signal (block 40), so that the drive signal is a closer match to the action of the device, e.g. so that the frequency of the drive signal matches the natural resonant frequency of the device. The amplitude of the drive signal can also be adjusted to produce a desired workpiece amplitude.

The above steps are repeated at regular intervals to ensure constant updates on system performance. The benefit of the above system is quite significant, as in addition to providing a simple and reliable means for making adjustments to the drive signal in accordance with system performance, there is no need for a separate sensing element. Also, the manufacturing tolerances for the individual components can be relaxed significantly. Further, there is no longer any need for an accurate clock (requiring a high quality crystal or ceramic resonator) to drive the circuit, or a highly accurately produced brushhead member. This reduces the cost of the appliance. Further, if the interruption of the drive signal is long enough, it can be detected by the user, which provides a confirmation of the special operation of the system.

Although a preferred embodiment has been disclosed for purposes of illustration, it is should be understood that various changes, modifications and substitutions may be incorporated in the embodiment without departing from the spirit of the invention, which is defined by the claims which follow.

What is claimed is:

1. A system for determining the resonant frequency and/or amplitude of an oscillating appliance, such as a toothbrush, having a drive assembly with a stator portion and an armature portion and a circuit for supplying a driving signal to the stator portion, comprising:
    a control circuit for temporarily interrupting the driving signal from the stator portion of the drive assembly for a selected period of time, wherein the selected period of time is long enough that a sufficient signal is induced into the stator, by continuing movement of the armature following interruption of the driving signal, that the frequency and/or amplitude of the induced signal can be determined; and
    a measurement circuit for determining at least one of: (1) the frequency of the induced signal; and (2) the amplitude of the induced signal, wherein the induced signal provides useful information concerning operation of the appliance.

2. A system of claim 1, including a comparison circuit for comparing the determined frequency or amplitude of the measured signal against an established value, to determine differences therebetween, and then altering the driving signal in accordance with said differences.

3. A system of claim 2, wherein the frequency measurement is accomplished by a zero crossing circuit.

4. A system of claim 2, wherein the frequency measurement is accomplished using a peak detector circuit.

5. A system of claim 2, wherein the control circuit interrupts the driving signal at preselected intervals during operation of the oscillating appliance.

6. A system of claim 2, wherein the frequency measurement is accomplished using a reference voltage crossing circuit.

7. A system of claim 2, wherein the frequency measurement is accomplished using a similar slopes circuit.

8. A system of claim 2, including an analog to digital converter for converting the measured signal information to digital information and a circuit for determining damping characteristics and Q of the appliance therefrom.

9. A system of claim 2, including an analog to digital converter for converting sufficient measured analog induced signal information to digital information to produce a sine wave signal and for comparing the sine wave signal against a pre-established sine wave to provide selected performance information of the appliance.

10. A system of claim 1 wherein the appliance is a toothbrush.

11. A method for determining the frequency and/or amplitude of an oscillating apparatus which has a drive assembly with a stator portion and an armature portion and a circuit for applying a driving signal to the stator portion, comprising the steps of:
    interrupting the application of the driving signal in the stator portion for a selected period of time, at least for one-half cycle of the driving signal, resulting in a signal being induced into the stator from movement of the armature following interruption of the driving signal;
    determining at least one of: the frequency of the induced signal and the amplitude of the induced signal, wherein the induced signal provides useful information concerning the operation of the device;
    comparing the determined frequency and/or amplitude with pre-established values and determining any differences therebetween; and
    changing the driving frequency/amplitude of the drive signal in accordance with said differences.

12. A method of claim 11, wherein the frequency is determined using a zero crossing circuit.

13. A method of claim 11, wherein the frequency is determined using a peak detector circuit.

14. A method of claim 11, wherein the frequency measurement is accomplished using a response voltage crossing circuit.

15. A method of claim 11, wherein the frequency measurement is accomplished using a similar slopes current.

16. A method of claim 11, including the step of converting analog measured information of the induced signal to digital information and then using the digital information to obtain additional information concerning performance of the appliance.

* * * * *